United States Patent [19]

Pankhania et al.

[11] Patent Number: 4,831,058

[45] Date of Patent: May 16, 1989

[54] THERAPEUTIC AGENTS

[75] Inventors: Mahendra G. Pankhania; Colin J. Lewis, both of Nottingham, England

[73] Assignee: Boots Company PLC, Nottingham, England

[21] Appl. No.: 102,863

[22] Filed: Sep. 30, 1987

[30] Foreign Application Priority Data

Oct. 1, 1986 [GB] United Kingdom ............... 8623557

[51] Int. Cl.$^4$ ............................................. A61K 31/19
[52] U.S. Cl. ..................................... 514/570; 514/557
[58] Field of Search .................... 514/576, 557, 570

[56] References Cited

U.S. PATENT DOCUMENTS 3,636,200  1/1972  Zentner et al. .
4,716,033  12/1987 Denick, Jr. .

FOREIGN PATENT DOCUMENTS 0069097  1/1983   European Pat. Off. .
0094116  11/1983  European Pat. Off. .
0219458  9/1986   European Pat. Off. .
1435892  7/1972   United Kingdom .
1394391  5/1975   United Kingdom .
1451541  10/1976  United Kingdom .
1527563  10/1978  United Kingdom .
2003028  3/1979   United Kingdom .
2079600  1/1982   United Kingdom .
2154233  9/1985   United Kingdom .

OTHER PUBLICATIONS

Chem. Abstr. 107-32629F (1987).
Derwent Abstract of J55129224.
Derwent Abstract of J58213710.

*Primary Examiner*—Stanley J. Friedman
*Attorney, Agent, or Firm*—Donald A. Peterson; Herbert D. Hart, III

[57] ABSTRACT

A pharmaceutical composition for oral administration comprising a mixture of ibuprofen or a pharmaceutically acceptable salt thereof and aluminium hydroxide, the amount of aluminium hydroxide being sufficient to mask the bitter taste of the ibuprofen, or the salt thereof which would be evident in the absence of aluminium hydroxide.

The ratio of aluminium hydroxide (expressed as equivalent aluminium oxide) to ibuprofen may be in the range 1:50 to 5:1 parts by weight.

23 Claims, No Drawings

THERAPEUTIC AGENTS

FIELD OF THE INVENTION

The present invention relates to pharmaceutical compositions for oral administration in which the disagreeable taste of ibuprofen or a salt thereof is masked by the incorporation of aluminium hydroxide in the compositions.

BACKGROUND OF THE INVENTION

Description of the Related Art

Ibuprofen, the chemical name of which is 2-(4-isobutylphenyl)propionic acid, is a well known medicament with anti-inflammatory, antipyretic and analgesic activities. The uses of ibuprofen include the treatment of pain and inflammation in musculoskeletal disorders such as rheumatic disease, and the treatment of pain in a variety of other disorders, for example headache, neuralgia and dysmenorrhoea.

Ibuprofen and certain salts thereof, for example, the sodium salt, have a disagreeable taste. Accordingly, when tablets of ibuprofen are required for direct oral administration, they are generally coated, for example, with a sugar coating, so that the patient does not experience the disagreeable taste.

European patent application No. 94116 discloses therapeutic enteric-coated granules comprising (a) a non-steroidal, therapeutic active core, (b) a first coating adhered to said core containing a non-steroidal therapeutic active and a dispersing material, and (c) a second coating adhered to said first coating of an enteric material. The application discloses that the invention is applicable to numerous therapeutic actives, including ibuprofen. The dispersing material included in the first coating aids in the disrupting of the enteric coating in the intestines. It is disclosed that the dispersing material affects the pH of the environment and may be selected from a wide variety of materials, including aluminium hydroxide. The preferred dispersing materials are the alkali metal phosphate salts and glycine. This patent application does not disclose nor suggest that the disagreeable taste of ibuprofen or a salt thereof can be masked by the incorporation of aluminium hydroxide in a composition.

It is also known (see for example UK Patent Specifications Nos. 1,527,563, 2,003,028B and 2,079,600B) that aluminium salts of ibuprofen do not have a disagreeable taste and the use of aluminium salts of ibuprofen in a variety of pharmaceutical formulations has been proposed. However, it is desirable to find an excipient which may simply be added to compositions containing ibuprofen to overcome the undesirable taste, without involving the preparation of different salts of ibuprofen which may have a different or modified therapeutic activity from those pharmaceutically acceptable salts which are of recognized utility, or without involving complex formulation stages.

Summary of the Invention

It has now been found that the undesirable taste of ibuprofen in pharmaceutical compositions can be overcome by incorporating a single excipient, namely aluminium hydroxide, in the compositions. An object of the present invention is to provide an ibuprofen formulation in which the undesirable taste associated with ibuprofen is masked and which avoids the necessity of (a) forming aluminium salts of ibuprofen, (b) of providing compositions presented in the form of microcapsules or (c) of involving other complex formulation processes, in order to produce ibuprofen compositions having an acceptable taste.

Accordingly in one broad form the present invention includes a pharmaceutical composition for oral administration, comprising a mixture of ibuprofen or a pharmaceutically acceptable salt thereof and aluminium hydroxide, the amount of aluminium hydroxide being sufficient to mask the taste of the ibuprofen or the salt thereof, which would be evident in the absence of the aluminium hydroxide.

The present invention also includes the aforesaid composition in liquid or suspension form as well as solid compositions such as capsules, tablets and powders.

The present invention also includes a dosage unit form of an intimate mixture of aluminium hydroxide and ibuprofen or a pharmaceutically acceptable salt thereof.

The present invention also includes a method of treating inflammation in a mammalian subject, including humans and animals, which comprises administering to said subject having an inflammatory condition, an anti-inflammatory effective amount of ibuprofen or a pharmaceutically acceptable salt thereof and an amount of aluminium hydroxide sufficient to mask the taste of ibuprofen or a salt thereof.

The present invention also includes a method of effecting analgesia in a mammalian subject, including humans and animals, which comprises administering to said subject in need thereof an analgesically effective amount of ibuprofen or a pharmaceutically acceptable salt thereof and an amount of aluminium hydroxide sufficient to mask the taste of ibuprofen or the salt thereof.

This invention also includes a method of masking undesirable taste of a pharmaceutical composition comprising a therapeutically effective amount of ibuprofen or a pharmaceutically acceptable salt thereof which method comprises adding a taste-masking amount of aluminium hydroxide to the said composition.

Also included as a part of the invention is a process to prepare a composition having a minimal undesirable taste as wherein ibuprofen or a pharmaceutically acceptable salt thereof is combined with a taste masking amount of aluminium hydroxide to form a mixture having an acceptable taste and suitable for mammalian and/or human ingestion.

Detailed Description of the Invention and Specific Embodiments

It has been found that the taste of ibuprofen in compositions containing aluminium hydroxide is masked. In some cases a masking effect is observed when only very small quantities of aluminium hydroxide are incorporated in the composition. As well as overcoming the undesirable taste of ibuprofen, compositions according to the invention have an acceptable appearance and are stable on storage. In addition compositions according to the present invention do not require complex formulation processes. Aluminium hydroxide may generally be incorporated into ibuprofen compositions by combining with other formulation excipients and forming the composition into any desired presentation e.g. dispersion in an aqueous base, or compression to form a tablet. This provides a significant cost advantage over compositions where the ibuprofen requires to be modified to produce a composition having an acceptable taste.

It will be appreciated that reference herein to ibuprofen includes a reference to the pharmaceutically acceptable salts of ibuprofen with a disagreeable taste, for example, the sodium salt.

The compositions of the present invention generally contain an orally acceptable carrier which may be a solid material, a liquid material, or a mixture thereof, depending on the type of composition desired.

Suitably ibuprofen and aluminium hydroxide are combined to form a substantially uniform mixture. Preferably the ibuprofen, aluminium hydroxide and the orally acceptable pharmaceutical carrier are intimately combined to provide a homogeneous mixture. This may take the form of a uniform blend of pharmaceutically active ingredient, aluminium hydroxide and carrier, for example, a uniform dispersion or suspension of the ingredients in a solid or liquid medium. In a preferred embodiment of the invention, the composition is in solid form wherein the ingredients have been thoroughly mixed to form an intimate admixture and compressed to form a tablet.

The compositions of the present invention may take any of the known pharmaceutical forms for oral administration, for example tablets (particularly chewable tables, effervescent tablets and dispersible tables), granules including dispersible granules and effervescent granules, and other solid dosage forms, including capsules. Especially advantageous characteristics are observed when aluminium hydroxide is incorporated in solid compositions dispersible in water e.g. tablets or granules. The compositions may also be in liquid form, for example aqueous suspensions and syrups. Aqueous suspensions of ibuprofen have been found to have particularly valuable advantages in taste over previously known ibuprofen suspensions.

Preparations of aluminium hydroxide in common use in pharmacy are Aluminium Hydroxide Gel BP (also known as Aluminium Hydroxide Mixture BP), and Dried Aluminium Hydroxide Gel BP (also known as Dried Aluminium Hydroxide BP). If desired the Dried Aluminium Hydroxide Gel BP can be formulated with water and formed into aluminium hydroxide paste. Aluminium Hydroxide Gel BP is in the form of an aqueous suspension and Dried Aluminium Hydroxide Gel BP is in the form of a powder. Such forms contain varying amounts of aluminium hydroxide and may also contain basic aluminium carbonate and bicarbonate (see the British Pharmacopoeia 1980, page 684-5 for a description of Aluminium Hydroxide Gel BP, and the British Pharmacopoeia 1980, addendum 1986, page 352 for a description of Dried Aluminium Hydroxide Gel BP. Another description of the aluminium hydroxide may be found in the United States Pharmacopoeia, vol. XXI, pages 30-31, of Aluminium Hydroxide Gel USP and Dried Aluminium Hydroxide Gel USP).

It is convenient to express the quantity of aluminium hydroxide in pharmaceutical preparations in terms of the equivalent content of aluminium oxide. For example, the British Pharmacopoeia (BP) 1980, requires that Aluminium Hydroxide Gel BP has an equivalent aluminium oxide content of not less than 3.5% w/w and not more than 4.4% w/w, and the British Pharmacopoeia 1980, addendum 1986 requires that Dried Aluminium Hydroxide Gel BP has an equivalent aluminium oxide content of not less than 47% w/w and not more than 60% w/w. As a further example, the United States Pharmacopeia, Vol XXI, (USP) requires that each 100g of Aluminium Hydroxide Gel USP contains the equivalent of not less than 3.6g and not more than 4.4g of aluminium oxide in the form of aluminium hydroxide and hydrated oxide and it may contain varying quantities of basic aluminium carbonate and bicarbonate; it further requires that Dried Aluminium Hydroxide Gel USP yields not less than 50% and not more than 57.5% aluminium oxide in the form of hydrated oxide, and it may contain varying quantities of basic aluminium carbonate and bicarbonate. For convenience in defining the compositions, weights and ratios of aluminium hydroxide are expressed hereinafter in terms of their aluminium oxide equivalent.

The amount of aluminium hydroxide that may be employed in a composition according to the invention may vary within wide limits. The useful upper limit is the level which would provide toxic or generally undesirable side effects when administered to a patient. The lower limit may be determined by the quantity of flavourings or other additives also used, as such excipients also act to mask the taste of ibuprofen to varying degrees. Where a large quantity of flavourings or other additives is employed, the amount of aluminium hydroxide employed may be minimal. Conversely, when aluminium hydroxide is added to a composition containing ibuprofen, the composition has an agreeable taste with a reduced level of flavourings. Suitably up to 1 g aluminium hydroxide may be employed per dose. The amount of aluminium hydroxide incorporated in the composition is an amount which masks the taste of ibuprofen. The taste-masking amount can be determined by a simple taste comparison between two similar ibuprofen dosage forms, one containing aluminium hydroxide and one without aluminium hydroxide. It is necessary to incorporate aluminium hydroxide to an extent where there is a discernible difference in the tastes between the two compositions. Suitably, aluminium hydroxide is incorporated to an extent to produce an acceptable taste. The masking of the taste of ibuprofen provides that the patient does not experience a significant bitter or unpleasant taste whilst the dosage form is in the mouth, or that he does not experience a significant tingling or burning sensation in the throat after swallowing the composition. Preferably, the aluminium hydroxide is present in an amount to reduce the unpleasant taste and the sensation in the throat to an acceptable level. It will be appreciated that the agreeable taste can be supplemented by flavouring components.

Valuable compositions according to the present invention comprise aluminium hydroxide up to an extent of 20% by weight of the composition, for example from 0.1 to 20% by weight (expressed as equivalent aluminium oxide). Preferred compositions comprise from 0.1 to 10% by weight aluminium hydroxide, especially 0.5 to 5% by weight (expressed as equivalent aluminium oxide). For example, when the composition is presented in solid form, the composition advantageously comprises aluminium hydroxide in the range of 0.1-5% by weight of the composition, particularly 0.5-2% by weight (expressed as equivalent aluminium oxide). When the formulation is presented in liquid form the formulation advantageously comprises 0.1-15g aluminium hydroxide per 100 ml of the formulation, particularly 0.1-5g per 100 ml, (expressed as equivalent aluminium oxide).

Conveniently aluminium hydroxide is employed to an extent of up to 5 parts by weight aluminium hydroxide (expressed as equivalent aluminium oxide) per 1 part by weight ibuprofen. The ratio of aluminium hydroxide (expressed as equivalent aluminium oxide) to ibuprofen may fall in the range 1:50 to 5:1 parts by weight, particularly 1:40 to 5:1 parts by weight, desirably 1:30 to 5:1 parts by weight. Suitable ratios of aluminium hydroxide (expressed as equivalent alumium oxide) to ibuprofen in a composition according to the invention lie in the range 1:30 to 3:1 parts by weight, more usually 1:20 to 3:1 parts by weight, and preferably 1:10 to 2:1 parts by weight. Advantageous ratios of aluminium hydroxide (expressed as equivalent aluminium oxide) to ibuprofen within the range 1:10 to 2:1 include 1:8, 1:6, 1:4 and 1:3 parts by weight. The preferred weight ratios of aluminium hydroxide (expressed as equivalent aluminium oxide) to ibuprofen for oral liquid dosage forms lie in the range of 1:5 to 1:1, especially 1:2 to 1:1. The aluminium hydroxide may be provided in the compositions of this invention by a precursor therefor. For example, aluminium oxide may be substituted at an equivalent level to aluminium hydroxide where suitable conditions prevail to allow the aluminium oxide to hydrate. If desired, a proportion of the aluminium hydroxide may be replaced by salts of aluminium for example aluminium phosphate and aluminium glycinate, coprecipitates of aluminium hydroxide and complex compounds containing aluminium oxide which may be hydrated e.g. Magaldrate USP (hydrated magnesium aluminate) and Hydrotalcite (aluminium magnesium carbonate hydrate).

The compositions of this invention include ibuprofen or any of its pharmaceutically acceptable salts. Some salts of ibuprofen have a more acceptable taste than ibuprofen itself. Nevertheless, advantageous properties may also be obtained by the inclusion of aluminium hydroxide in a composition containing salts of ibuprofen, in particular the sodium, potassium, magnesium and calcium salts of ibuprofen.

Ibuprofen or a pharmaceutically acceptable salt thereof is employed to an extent in a composition according to the present invention to provide a therapeutically effective level. Most compositions contain 1-95% by weight ibuprofen. Tablets containing ibuprofen generally contain up to 90% by weight, for example 10-90% by weight ibuprofen, particularly 10 to 70% by weight. Solid forms arranged to effervesce or disperse when in contact with water to produce a suspension may contain a lower amount of ibuprofen. Preferred solid dispersible compositions contain 10-40% by weight, especially 15 to 30% by weight ibuprofen. Suitably liquid compositions may comprise up to 50g ibuprofen per 100 ml composition, for example 1 to 50g, preferably 1-10g, and especially from 1-5g ibuprofen per 100 ml composition. Preferred compositions according to the invention comprise ibuprofen in an amount of 1 to 50% by weight of the composition, more preferably 1 to 25% by weight of the composition.

The orally acceptable pharmaceutical carrier which may be employed in a composition according to the invention is determined by the form in which it is desired to present the composition. It will generally comprise from 1-99% by weight of the composition, especially 50-99% by weight of the composition. Suitable excipients useful for solid and liquid dosage forms will be appreciated by those skilled in the art. The examples of suitable materials listed below are illustrative of the well known examples.

Where it is desired to present the composition in a solid form, any of the known orally acceptable solid carriers may be employed for example binders, soluble and insoluble diluents, lubricants, flow aids, accelerants and disintegrants. Examples of binders include polyvinylpyrrolidone, microcrystalline cellulose, gelatin and gums. In general binders may comprise up to 20% by weight of the composition. Examples of soluble diluents include lactose, sodium chloride, dextrins and sorbitol and examples of insoluble diluents include microcrystalline cellulose, calcium sulphate and di- and tri- calcium phosphate. Diluents may be used by up to 50% by weight of the composition. Also there may be added to the composition up to 5% by weight of lubricants, for example stearic acid, polyethylene glycol 6000, magnesium stearate; up to 5% by weight of flow aids such as colloidal silica and talc; and up to 30% by weight accelerants and disintegrants for example vegatable starches and starch derivatives, cellulose, cellulose derivatives and modified cellulose derivatives; also surfactants, e.g. sodium lauryl sulphate and Tween 80, flavourings and other oils, fats and waxes may be added as desired. Especial advantages have been found by using one or more of the following excipients in solid dosage forms: microcrystalline cellulose, croscarmellose sodium, silica, sodium lauryl sulphate and stearic acid. A preferred solid composition according to the invention is a compositin dispersible in water, accordingly such a dosage form contains a significant proportion of disintegrants especially cellulose or modified cellulose derivatives, for example microcrystalline cellulose.

Where a composition according to the invention is presented in the form of a liquid the orally acceptable pharmaceutical carrier may include one or more of the following: water, alcohols and polyols, wetting and emulsifying agents, suspending and thickening agents, humectants, preservatives, flavourings and colouring agents. Examples of wetting and emulsifying agents include sodium lauryl sulphate, sorbitan esters and Cremophor (trade name). These agents may comprise up to 5% by weight of the composition. The composition may comprise up to 70% by weight of suspending and thickening agents, for example sugar, gums, celluloses and cellulose derivatives; up to 20% by weight preservatives, for example parabens, benzoates, bronopol and ethyl alcohol; up to 30% by weight humectants for example sorbitol and glycerin; and also flavourings and colouring agents as desired. Especial advantages have been found by using one or more of the following excipients: sorbitol, glycerin, sucrose, carrageenan gum, microcrystalline cellulose and water.

The compositions according to the invention may be prepared in unit dosage form. Such dosage units suitably contain 50-1200 mg, more usually 200-800 mg ibuprofen or the therapeutic equivalent of a pharmaceutically acceptable salt of ibuprofen. The dosage as employed for an adult human treatment is generally in the range from 100 to 3200 mg per day.

Compositions according to the invention may be prepared by a variety of processes depending on the desired form of presentation. Suitably ibuprofen is combined with aluminium hydroxide to form a mixture. Preferably the mixture is combined with an orally acceptable pharmaceutical carrier. Conveniently, aluminium hydroxide may be added to the ibuprofen, optionally with excipients, in the form of a paste or as a dried gel, and the mixture combined with the carrier until a uniform mixture of ibuprofen and aluminium hydroxide in the carrier is obtained.

One method of forming liquid compositions according to the invention using an aqueous carrier is to form a homogeneous paste of aluminium hydroxide, ibuprofen and a surfactant and then add it to a solution of the remaining excipients in water. The paste may be prepared by mixing Dried Aluminium Hydroxide Gel BP with a small amount of water and optionally a surfactant to form a paste having a suitable viscosity.

One method of forming solid compositions according to the invention is to granulate ibuprofen, optionally with flow aids, diluents and binders etc. using an aqueous or non-aqueous granulating fluid. The wet granulate is dried, sized and then blended with Dried Aluminium Hydroxide Gel BP and other necessary excipients such as flow aids, lubricants and disintegrants. The blended granules are then compressed using suitable tooling to give tablets of the correct weight and ibuprofen content. Alternatively, Dried Aluminium Hydroxide Gel BP may be included at the granulation step by blending with ibuprofen and optional diluents prior to the addition of the granulating fluid.

The invention is illustrated by the following non-limitative Examples.

In the Examples the carrageenan gum is available from Hercules, Salford, England under the trade name Genuvisco J; the microcrystalline cellulose is available from FMC Corporation, Philadelphia, USA under the trade name Avicel; the croscarmellose sodium is available from FMC Corporation, Philadelphia, USA under the trade name Ac-Di-Sol; the fumed silica is available from Degussa, West Germany under the trade name Aerosil; Polysorbate 80 BP is available from Atlas Chemicals, Leatherhead, UK under the trade name Tween 80; the bronopol is available from The Boots Company, Nottingham, England.

EXAMPLE 1

| Ingredients | Quantity % w/v |
|---|---|
| Light Magnesium Oxide | 1.19 |
| Magnesium Sulphate BP Super Pearl | 0.015 |
| Carrageenan gum (Genuvisco J) | 0.35 |
| Aluminium Hydroxide Paste | 4.1[1] |
| Sodium Citrate BP | 0.01 |
| Bronopol | 0.01 |
| Sodium Saccharin BP Pdr | 0.03 |
| Flavourings | 0.08 |
| Colourings | 0.002 |
| Ibuprofen | 2.0 |
| Purified Water BP to | 100 |

Notes
[1]Expressed as equivalent aluminium oxide

The ibuprofen suspension was prepared in the following manner. Cream of magnesia was prepared by mixing the magnesium oxide and the magnesium sulphate with water. This product was added to the carrageenan gum into which the aluminium hydroxide paste and ibuprofen had already been thoroughly mixed. The remaining additives were added with stirring and made up to volume.

The composition of Example 1 was found to have a more acceptable taste than the corresponding composition without the aluminium hydroxide component.

EXAMPLE 2

| Ingredients | Quantity % w/v |
|---|---|
| Ibuprofen | 2.0 |
| Bronopol | 0.01 |
| Sodium Saccharin BP | 0.3 |
| Sodium Citrate BP | 1.0 |
| Carrageenan gum (Genuvisco J) | 0.5 |
| Aluminium Hydroxide Paste | 0.5[1] |
| Spearmint Flavour | qs |
| Purified Water BP to | 100.0 |

Notes:
[1]Expressed as equivalent aluminium oxide.

The suspension was prepared by mixing aluminium hydroxide paste with the ibuprofen and a small quantity of purified water until a smooth cream was formed. This cream was added to a gel of the carrageenan gum prepared in purified water. The bronopol and the remaining ingredients were added and the suspension made up to volume.

The composition of Example 2 was found to have a more acceptable taste than the corresponding composition without the aluminium hydroxide component.

EXAMPLE 3 Ibuprofen Dispersible Tablets

| Ingredients | Quantity % w/w |
|---|---|
| Ibuprofen | 19.3 |
| Microcrystalline cellulose (Avicel PH 101) | 63.1 |
| Croscarmellose sodium (Ac-Di-Sol) | 10.6 |
| Fumed silica (Aerosil 300) | 0.5 |
| Dried Aluminium Hydroxide Gel BP | 2.0[1] |
| Sodium Lauryl Sulphate | 1.5 |
| Stearic Acid BP Pdr | 2.0 |
| Menthol Flavour | 1.0 |

Notes:
[1]Equivalent aluminium oxide = 1% w/w

The ibuprofen, a portion of the microcrystalline cellulose and a portion of the croscarmellose sodium were granulated using isopropyl alcohol and then sized and dried. The dry granulate was sized and blended with the remaining excipients and compressed into tablets.

The composition of Example 3 was found to have a more acceptable taste than the corresponding composition without the aluminium hydroxide component.

EXAMPLE 4

| Ingredients | Quantity % w/v |
|---|---|
| Ibuprofen | 4 |
| Dried Aluminium Hydroxide Gel BP | 5[1] |
| Carrageenan gum (Genuvisco J) | 0.8 |
| Methyl Hydroxy Benzoate BP | 0.1 |
| Propyl Hydroxybenzoate BP | 0.05 |
| Sodium Benzoate BP | 0.25 |
| Sodium Saccharin BP | 0.3 |
| Sorbitol Sol. BPC | 10.0 |
| Glycerin BP | 15.0 |
| Purified Water BP to | 100 |

Notes:
[1]Equivalent aluminium oxide content = 2.5% w/v

The ibuprofen was admixed with the Dried Aluminium Hydroxide Gel and some of the water to form a paste. The benzoates were dissolved in the remainder of the water with heating to 90° C. The dried carrageenan gum was then added and dispersed and dissolved in the water to form a gel, followed by the addition of the remaining materials. The paste containing aluminium hydroxide and ibuprofen was stirred into the gel suspension until a homogeneous suspension was obtained.

The composition of Example 4 was found to have a more acceptable taste than the corresponding composition without the aluminium hydroxide component.

EXAMPLE 5

| Ingredient | Quantity % w/v |
|---|---|
| Ibuprofen | 2.0 |
| Methyl Hydroxybenzoate BP | 0.1 |
| Propyl Hydroxybenzoate BP | 0.05 |
| Sodium Saccharin BP | 0.3 |
| Sorbitol BPC | 10.0 |
| Glycerin BP | 15.0 |
| Sodium Benzoate BP | 0.25 |
| Microcrystalline cellulose (Avicel CL611) | 2.5 |
| Dried Aluminium Hydroxide Gel BP | 2.0[1] |
| Colourings and Flavourings | qs |
| Purified Water BP to | 100.0 |

Notes:
[1]Equivalent aluminium oxide content = 1% w/v

The ibuprofen was admixed with the Dried Aluminium Hydroxide Gel together with some of the water to form a paste. The benzoates were dissolved in the remainder of the water with heating to 90° C. The microcrystalline cellulose was then added and dispersed in the water to form a gel, followed by the addition of the remaining materials. The paste containing aluminium hydroxide and ibuprofen was stirred into the gel suspension until a homogeneous suspension was obtained.

The composition of Example 5 was found to have a more acceptable taste than the corresponding composition without the aluminium hydroxide component.

EXAMPLE 6

| Ingredients | Quantity % w/v |
|---|---|
| Ibuprofen | 2.0 |
| Dried Aluminium Hydroxide Gel BP | 2.0[1] |
| Methyl Hydroxybenzoate BP | 0.1 |
| Propyl Hydroxybenzoate BP | 0.05 |
| Sucrose BP | 66.0 |
| Sodium Benzoate BP | 0.25 |
| Agar BPC 54 | 0.3 |
| Glycerin BP | 10.0 |
| Sorbitol BPC | 10.0 |
| Polysorbate 80 BP (Tween 80) | 0.1 |
| Colourings and Flavourings | qs |
| Purified Water BP to | 100.0 |

Notes:
[1]Equivalent aluminium oxide content = 1% w/v

The ibuprofen was admixed with the Dried Aluminium Hydroxide Gel, the polysorbate 50 BP and some of the water to form a paste. The benzoates were added to the remainder of the water with heating to 90° C., followed by the addition of the agar. The agar was dissolved to form a gel, into which the sucrose and other materials were dissolved. The aluminium hydroxide paste containing ibuprofen was stirred into the gel suspension until a homogeneous suspension was obtained.

The composition of Example 6 was found to have a more acceptable taste than the corresponding composition without the aluminium hydroxide component.

We claim:

1. A method of treating inflammation in a mammalian subject, including humans and animals, which comprises administering to said subject having an inflammatory condition, a substantially uniform mixture of an anti-inflammatory effective amount of ibuprofen or a pharmaceutically acceptable salt thereof and an amount of aluminum hydroxide sufficient to mask the taste of ibuprofen or the salt thereof.

2. A method of effecting analgesia in a mammalian subject, including human and animals, with comprises administering to said subject in need thereof, a substantially uniform mixture of an analgesically effective amount of ibuprofen or a pharmaceutically acceptable salt thereof and an amount of aluminum hydroxide sufficient to mask the taste of ibuprofen or the salt thereof.

3. A method of masking the taste of a pharmaceutical composition comprising a therapeutically effective amount of ibuprofen or a pharmaceutically acceptable salt thereof which comprises incorporating a taste-masking amount of aluminum hydroxide to form a uniform mixture with said composition.

4. A pharmaceutical composition for oral administration comprising a substantially uniform mixture of ibuprofen or a pharmaceutically acceptable salt thereof and aluminum hydroxide, the amount of aluminum hydroxide being sufficient to mask the taste of the ibuprofen or the salt thereof which would be evident in the absence of aluminum hydroxide.

5. A composition according to claim 4 wherein the ratio of aluminium hydroxide expressed as equivalent aluminium oxide to ibuprofen or a pharmaceutically acceptable salt thereof lies in the range from 1:30 to 3:1 parts by weight.

6. A solid composition according to claim 4 comprising from 0.1 to 5% by weight of the composition aluminium hydroxide expressed as equivalent aluminium oxide.

7. A solid composition according to claim 6 comprising from 10 to 40% by weight of the composition ibuprofen or a pharmaceutically acceptable salt thereof.

8. A solid composition according to claim 6 which is dispersible in water.

9. A liquid composition according to claim 4 comprising from 0.1 to 5g aluminium hydroxide expressed as equivalent aluminium oxide per 100 ml liquid composition.

10. A liquid composition according to claim 9 comprising from 1 to 10 g ibuprofen or a pharmaceutically acceptable salt thereof per 100 ml liquid composition.

11. A process to prepare a composition as claimed in claim 4 wherein ibuprofen or a pharmaceutically acceptable salt thereof is combined with a taste-masking amount of aluminium hydroxide to form a mixture having an acceptable taste and suitable for mammalian and/or human ingestion.

12. A stable pharmaceutical ibuprofen composition for oral administration to relieve an inflammatory condition or provide an analgesic effect in a subject which comprises an intimate admixture in unit dosage form of from 50 to 1200 mg ibuprofen or a pharmaceutically acceptable salt thereof and from 0.02 to 5 parts aluminium hydroxide per part of ibuprofen or salt thereof sufficient to mask the taste of said ibuprofen component which would be evident in the absence of aluminium hydroxide.

13. An ibuprofen composition according to claim 12 in the form of a compressed tablet.

14. An ibuprofen composition according to claim 12 in the form of an aqueous suspension.

15. A pharmaceutical composition for oral administration comprising a substantially uniform mixture of ibuprofen or a pharmaceutically acceptable salt thereof in an amount of 1 to 95% by weight of the composition and aluminum hydroxide, the ratio of aluminum hydroxide to ibuprofen being in the range of 1:30 to 3:1 parts by weight, said amount of aluminum hydroxide being sufficient to mask the taste of the ibuprofen or the salt thereof which would be evident in the absence of aluminum hydroxide.

16. A composition according to claim 15 comprising ibuprofen or a pharmaceutically acceptable salt thereof in an amount of 1 to 50% by weight of the composition.

17. A composition according to claim 16 wherein the ratio of aluminum hydroxide expressed as equivalent aluminum oxide to ibuprofen lies in the range from 1:20 to 3:1 parts by weight.

18. A composition according to claim 16 wherein the ratio of aluminum hydroxide expressed as equivalent aluminum oxide to ibuprofen lies in the range from 1:10 to 2:1 parts by weight.

19. A solid composition according to claim 16 comprising from 0.1 to 5% by weight of the composition of aluminum hydroxide expressed as equivalent aluminum oxide.

20. A solid composition according to claim 19 comprising from 10 to 40% by weight of the composition ibuprofen or a pharmaceutically acceptable salt thereof.

21. A solid composition according to claim 19 which is dispersible in water.

22. A liquid composition according to claim 16 comprising from 0.1 to 5g aluminum hydroxide expressed as equivalent oxide per 100 ml liquid composition.

23. A composition according to claim 15 comprising from 0.1 to 20% by weight of the composition of aluminum hydroxide expressed as equivalent aluminum oxide.

* * * * *